United States Patent [19]

Rosengren et al.

[11] 4,130,470

[45] Dec. 19, 1978

[54] METHOD FOR GENERATING A pH-FUNCTION FOR USE IN ELECTROPHORESIS

[75] Inventors: Ake Rosengren, Enskede; Bengt Bjellqvist, Stockholm; Vesna Gasparic, Nacka, all of Sweden

[73] Assignee: Aminkemi AB, Bromma, Sweden

[21] Appl. No.: 748,184

[22] Filed: Dec. 7, 1976

[30] Foreign Application Priority Data

Dec. 12, 1975 [SE] Sweden .................................. 7514049

[51] Int. Cl.$^2$ ............................................. G01N 27/26
[52] U.S. Cl. ............................ 204/180 G; 204/180 R; 204/299 R
[58] Field of Search ............... 204/180 G, 299, 180 R, 204/180 P

[56] References Cited

U.S. PATENT DOCUMENTS

| | | | |
|---|---|---|---|
| 2,731,411 | 1/1956 | Clarke | 204/180 P |
| 2,976,576 | 3/1961 | Wichterle et al. | 204/180 G X |
| 3,640,809 | 2/1972 | Polson et al. | 204/180 G |
| 3,692,654 | 9/1972 | Svendsen | 204/180 R |
| 3,704,217 | 11/1972 | Nerenberg | 204/180 G |
| 3,873,514 | 3/1975 | Chu et al. | 204/180 G X |
| 3,948,743 | 4/1976 | Monthony et al. | 204/180 G |

*Primary Examiner*—Arthur C. Prescott
*Attorney, Agent, or Firm*—George H. Mitchell, Jr.

[57] ABSTRACT

Method for changing the pH value of a compound used in electrophoresis which comprises the generating of the pH-function along at least part of the separation path from the protolysis equilibrium with the separation method and/or chargeable groups immobilized in a matrix, in which the groups contain one or more of the elements carbon, sulphur, phosphorus, boron, or nitrogen.

14 Claims, No Drawings

METHOD FOR GENERATING A PH-FUNCTION FOR USE IN ELECTROPHORESIS

The present invention refers to a method for generating a pH-function for use in electrophoretic separations.

In a variety of separation- and analytical methods, preferably electrophoretic methods it is required that the pH values as well as the temperature values are well controlled along a convection stabilized separation path. Hitherto the pH-functions used in electrophoretic methods have been obtained by means of different types of low molecular weight buffer solutions with a concentration of at least $10^{-2}M$ and usually considerably higher. These concentrations give rise to a considerable electrical conductivity and corresponding currents and thus relatively low field strength could be used if the temperature is to be maintained at a constant value. Since the time required for the separation is inversely proportional to the field strength this is a big disadvantage. In order not to change the pH value along the separation path during the experiment due to electrode reactions in the buffer vessels anode and cathode solutions of relatively high volumes are used, these vessels containing the same buffering substances as those used along the separation path.

Electrofocusing is an electrophoretic separation method for proteins and other ampholytes based on the fact that amphoteric substances subject to an electrical field migrate electrophoretically in a pH gradient towards the point, the so-called isoelectric point in the gradient where their net mobility is zero. Several methods are known for generating the pH-gradient necessary for the electrofocusing. The most important method is based on the use of a mixture of ampholytes, so-called carrier ampholytes, containing a high number of components with different pI-values (the pH-value at the isoelectric point), distributed along the pH range of interest. By means of the ion transport generated by the applied electrical field these carrier ampholytes generate the pH-function in which the separation is performed.

As in all electrophoretical methods it is of general interest to reduce the separation time in electrofocusing. In electrofocusing experiments where the pH gradient is generated from carrier ampholytes, the pH gradient has to be built up and the sample substances have to be transported towards their respective isoelectric points. The forming of a pH gradient and the transportation of the sample substances to their isoelectric points is made faster if the applied voltage and thus the field strength are increased. The possibility of applying high voltages is limited by the fact that the power generated in the system has to be cooled away. The main part of the current transport during the forming of the pH gradient as well as during later stages is performed by the carrier ampholytes and only a fraction of the current transport is related to the sample. Thus, a pH gradient, the forming of which and maintaining of which would not require any current transport would thus make it possible to reduce considerably the time required for the electrofocusing. Furthermore, the distinctiveness of the zone boundaries obtained at electrofocusing is increased with the field strength. An increase of the applied voltage would thus also result in an increase of the resolution to be obtained.

The pH gradients based on carrier ampholytes also have other disadvantages. Existing methods for producing synthetic carrier ampholytes for general analytical and separative use result in ampholyte mixtures having considerable variations in their conductivity and concentration in the pH gradient formed.

The appearance of the pH gradient will also vary with respect to time and a flow distortion of the pH gradient results in a movement of the sample zone.

When generating pH gradients to cover a limited pH range the number of individual ampholytes within this range also tend to be small in this type of ampholyte mixtures.

In order to obtain heavy disturbances in pH gradients based on carrier ampholytes the sample must not contain too big amounts of salt. In preparative electrofocusing, the electrofocusing must also be followed by a preparation stage where the sample components are released from the carrier ampholytes.

It is an object of the present invention to provide a new method for generating a pH function — preferably to be used in electrophoresis or electrofocusing, whereby the above discussed disadvantages are eliminated. The characteristics of the invention will appear from the claims enclosed with the specification.

According to the invention the pH function is formed by non-mobile charged or chargeable groups. Chargeable groups thereby comprise such groups that through protolysis equilibriums in relation to the used separation medium can give positive or negative net charges. The chargeable groups contain one or several of the elements carbon (C), sulphur (S), phosphorus (P), boron (B) or nitrogen (N). As an example of negatively chargeable groups could be mentioned carbon acid- (carbonic acid), sulphonic acid-, boron acid-(boric acid), or phosphon acid (phospho acid or phosphonic acid) groups as well as acid esters of polyvalent acids. The positively chargeable groups could consist of different types of amino groups or other chargeable nitrogen containing compounds.

The immobilization is achieved by means of affixing the groups to or into a matrix which could also constitute the convection stabilizing medium in the separation. This matrix could preferably be formed by a material which in combination with the separation medium gives rise to a gel. The immobilization means that no net transport of these charged or chargeable groups respectively is performed due to the applied outer electrical field. The mobility the groups may have because of the flexibility of the matrix structure use will not considerably affect the above described principle. By using several charged and/or chargeable groups the concentration of which varies along the field path, these groups can themselves or in combination with ampholytes be made to generate a pH function which is stable with respect to time and to be ambiguously varied along the separation path. The pH function could thereby be optimized with respect to the separation problem both in respect to the pH variation in the field direction and with respect to conductivity and buffering capacities.

As a separation medium one suitably chooses water or water in combination with some substance which is soluble in water or miscible with water. As a matrix a convection stabilizing system known per se could be used provided that this can be combined with a pH function according to the invention. The convection stabilizing system could for instance be granular, fibrous or by some other means be capillary stabilized or it could be formed by a gel. Examples of suitable material include polyacrylamide, cellulose, agarose, dextrane, polyvinylalcohol, starch, silicon gel or polymers of styrene divinyl benzene or combinations of those. The matrix could either be continuous from anode to cathode or be discontinuous, for instance by being constituted by membranes in multichamber electrolyzers. The latter is above all of interest in electrofocusing. It is however a requirement that ampholytes to be separated and/or added ampholyte give rise to a sufficient conductivity in the zones between the electrodes which are not filled up by a matrix containing non-mobile charged and/or chargeable groups.

Non-mobile chargeable or charged groups in the amount of $10^{-2}$ or $10^{-4}$ M per liter are enough to make the method work for generating the pH function according to the invention. In order to obtain sharp boundaries between the zones in the separation a certain buffering capacity is however necessary. It is suitable that the concentration of non-mobile charged or chargeable groups is not below $10^{-2}$ M per liter if the pH function is to be used in electrophoresis or electrofocusing without the carrier ampholytes. Each section of the convection stabilizing matrix could by the presence of the non-mobile groups be given a pH value. In order to obtain an optimum buffering capacity it is desirable that the non-mobile groups in a certain section of the matrix have pKs-values which are close to the pH value of the matrix section. The upper limit of the concentration of charged or chargeable groups is given by practical details such as the amounts of groups which could be made to be attached chemically in the matrix or the amount that the matrix could contain while maintaining the feature which makes it possible as a convection stabilizing medium in the separation in question.

For all the matrixes there are several known methods for incorporting charged or chargeable groups. Usable derivatives of polyacrylamide are suitably made by means of copolymerization. Almost all conjugated polar vinyl monomers copolymerize with acrylamide. By means of this method one thus obtains a big choice as to the charged and/or chargeable groups which could be immobilized in the matrix. An example of functional monomers which could be made to react into an acrylamide containing gel is vinyl sulphonate, acrylic acid, vinyl phosphon acrylamide acid, maleic acid, fumaric acid, itaconic acid, aconitic acid, vinyl pyridine, vinyl imidazole, allylamine, and diallylamine. Also functional derivatives of these compounds such as esters of the acids containing a suitable functional group, for instance amino alkyl acrylate could be made to copolymerize with acrylamide.

Certain of the above defined monomers could by using bisacryl amide or some other cross linking reagent be made to generate gels without having acrylamide as a component in the polymer. For generating of a pH function in polyacrylamide the polymerization is suitably performed in a conventional way in a water solution. For initiating the process peroxides, azo compounds, redox pairs, photochemical systems and/or ionizing radiation could be used. Some type of cross linking reagent could be included in the monomer mixture in order to make the co-polymer form a gel. A control variation of the concentration of the monomers involved could be obtained by means of conventional techniques, for instance by filling a vertically arranged polymerization chamber and having the gradient to be used in the focusing to coincide with a linear density gradient which is the necessary convection stabilizing gradient at the filling and furthermore counteracts a mixing derived from the heat generation of the polymerization.

If the convection stabilizing matrix exists initially, which for instance is the case with paper or cellulose acetate, compounds with suitable functional groups could be made to migrate into the matrix and generating a gradient and could thereafter be made to react so that immobilized charged or chargeable groups are obtained in the matrix. These could thereby be part of a polymer which is surrounded by the matrix or be part of a polymer or some other constellation which is chemically bound to the original matrix.

In electrophoretic analysis or separations using pH functions according to this invention one can keep conductivity low while maintaining a good buffering capacity. Thus, high field strength and thus short separation times are obtaind without any substantial generation of heat. Big amounts of electrode buffer volumes will not be necessary as with the present methods. Only small contact volumes or acid or base have to be used.

The pH function could easily be adapted for electrophoresis in discontinuous systems by changing the pH function in some part of the separation path or by changing both the pH function and the convection stabilizing matrix so as to give the charged molecules different mobilities in different parts of the separation path.

In electrofocusing in the pH function according to the invention one does also achieve said advantages as concerns fast separations and low heat development. Additionally, possibilities are obtained to generate the pH function in the form of pH gradient with an evenly distributed conductivity and buffering capacity. This has hitherto not been fully possible by using carrier ampholytes. The problem of movement of the pH gradient is eliminated by using the pH function and a big amount of salt in the sample could be permitted without disturbing the pH function. The separation could also be performed in continuous processes where the electrical field is perpendicular to a convection stabilized flow of the separation medium. The convection stabilizing could be performed with different methods known per se such as granular or fibrous systems in which the pH gradient is immobilized or some other capillary stabilized system where the flow stabilization is made in a slot between two adjacent surfaces on which the pH function is immobilized.

We claim:

1. Method for generating a pH function for use in electrophoresis, characterized in that the pH function at least along parts of the separation path is generated from the protolysis equilibriums with the separation medium of charged and/or chargeable groups immobilized to vary the pH function in a matrix along parts of the separation path with chemically affixed groups of various concentrations along said path to thereby prevent transport of said groups with respect to the matrix upon application of an outer electrical field, said groups containing one or several of the elements C, S, P, B or N.

2. Method according to claim 1, characterized in that the pH gradient is alternatively generated by the protolysis equilibrium with the separation medium of immobilized and not immobilized charged and/or chargeable functional groups.

3. Method according to claim 1, characterized in that the pH gradient could be monotonous or not monotonous within the pH interval 2–12 or parts of this range.

4. Method according to claim 1, characterized in that the matrix constitutes the convection stabilizing medium.

5. Method according to claim 4, characterized in that the matrix is formed by a gel.

6. Method according to claim 5, characterized in that the gel is a porosity gradient.

7. Method according to claim 4, characterized in that the matrix is granular.

8. Method according to claim 4, characterized in that the matrix is fibrous.

9. Method according to claim 1, characterized in that the matrix constitutes one or several surfaces in a capillary stabilized system.

10. Method according to claim 1, characterized in that the electrophoretic separation is made as a zone electrophoresis.

11. Method according to claim 1, characterized in that the electrophoretic separation is performed as an immunoelectrophoresis.

12. Method according to claim 1, characterized in that the electrophoretic separation is carried out as an electrofocusing.

13. Method according to claim 12, characterized in that the electrofocusing is performed in the presence of one or several not immobilized ampholines.

14. Method according to claim 2, characterized in that the matrix carrying the immobilized groups constitutes permeable membranes in a chamber electrolyser and that the pH function is general alternatively of these membranes and ampholytes.

* * * * *